United States Patent [19]

Coussediere et al.

[11] Patent Number: 4,873,256
[45] Date of Patent: Oct. 10, 1989

[54] ANTIANDROGENIC 4-HYDROXYMETHYL-2-IMIDAZOLIDINE-DIONES

[75] Inventors: Daniel Coussediere, Montfermeil; Giuseppe Gigliotti; Martine Moguilewsky, both of Paris, all of France

[73] Assignee: Roussel Uclaf, Paris, France

[21] Appl. No.: 230,587

[22] Filed: Aug. 10, 1988

[30] Foreign Application Priority Data

Aug. 13, 1987 [FR] France .................. 87 11544

[51] Int. Cl.[4] .................. A61K 31/415; C07D 233/78; C07D 233/88
[52] U.S. Cl. ...................................... 514/391; 548/313
[58] Field of Search .................. 548/313; 514/391

[56] References Cited

U.S. PATENT DOCUMENTS 3,651,079 3/1972 Skorcz et al. .................. 548/313
3,798,233 3/1974 Akiba et al. .................. 548/313 X
4,097,578 6/1978 Perronnet et al. .................. 548/314 X
4,473,393 9/1984 Nagpal .................. 548/313 X Primary Examiner—Richard A. Schwartz
Attorney, Agent, or Firm—Bierman & Muserlian

[57] ABSTRACT

A compound in all possible racemic and optically active forms of the formula

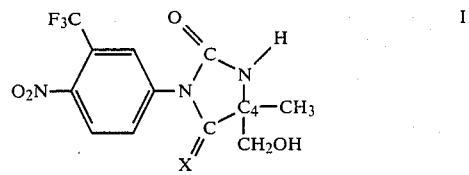

wherein =X is =O or imino having antiandrogenic activity and novel intermediates and processes for their preparations.

18 Claims, No Drawings

ANTIANDROGENIC 4-HYDROXYMETHYL-2-IMIDAZOLIDINE-DIONES

STATE OF THE ART 1-(3'-trifluoromethyl-4'-nitrophenyl)-4,4-dimethyl-imidazolidine-2,5-dione of the formula

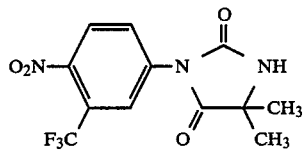

is described in French Pat. No. 2,329,276 published on the 27th of May, 1977 and has the code name of RU 23908, the common international denomination NILUTAMIDE and the trademark name ANANDRON ®. An article entitled "Pharmacology and Clinical Studies with 23908" (ANANDRON ®) in EORTC Genitourinary Group Monograph 2, part A: Therapeutic Principles in Metastatic Prostatic Cancer, pages 99 to 120, 1985 described particularly the supposed metabolites of 23908 in the rat. These metabolites of which the $NO_2$ group carried on the phenyl nucleus was reduced to NHOH or $NH_2$ all proved to be devoid of anti-androgen activity.

Also related prior art are U.S. Pat. Nos. 3,651,079 and No. 4,097,578 and European Pat. No. 0,091,596.

OBJECTS OF THE INVENTION

It is an object of the invention to provide the novel compounds of formula I and a novel process and intermediates for their preparation.

It is another object of the invention to provide novel antiandrogenic compositions and a novel method inducing antiandrogenic activity in warm-blooded animals.

These and other objects and advantages of the invention will become obvious from the following detailed description.

THE INVENTION

The novel compounds of the invention are a compound in all possible racemic and optically active forms of the formula

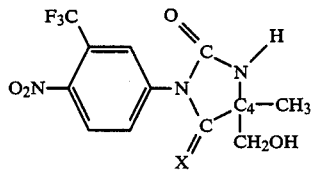   I wherein =x is =O or imino
The compound of the formula

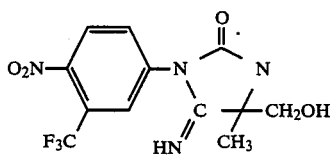

is an intermediate for the compound of the formula

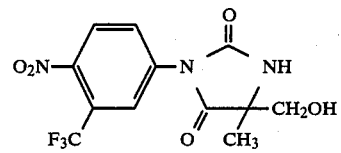   A which has an antiandrogenic activity.

These products have an asymmetric carbon in the 4-position and can be presented in racemic form as an equimolecular mixture of the two isomers or in the form of one of the isomers 4R or 4S, or of a non-equimolecular mixture of these two isomers. Product B is 4-(hydroxymethyl)-5-imino-4-methyl-1-[4-nitro-3-(trifluoromethyl)-phenyl]-2-imidazolidinone in racemic or optically active form and product A is 4-(hydroxymethyl)-4-methyl-1-[4-nitro-3-(trifluoromethyl)-phenyl]-2,5-imidazolidine dione in racemic or optically active form, and particularly, the racemic form. The products A in the form of their optically active isomers, namely (4R) 4-(hydroxymethyl)-4-methyl-1-[4-nitro-3-trifluoromethyl)-phenyl]-2,5-imidazolidine dione and the (4S) 4-(hydroxymethyl)-4-methyl-1-[4-nitro-3-trifluoromethyl)-phenyl]-2,5-imidazolidine dione are preferred. Also, 4-(hydroxymethyl)-4-methyl-1-[4-nitro-3-(trifluoromethyl)-phenyl]-2,5-imidazolidine dione may exist in the form of a mixture of its 4R and 4S isomers, a mixture differing from the 50—50 racemic mixture.

The novel process of the invention comprises reacting 2-amino-2-(hydroxymethyl)propane-nitrile in racemic or optically active form with 3-trifluoromethyl-4-nitrophenyl isocyanate to obtain a product of formula I wherein X is imino or 4-(hydroxymethyl-5-imino-4-methyl-1-[4-nitro-3-(trifluoromethyl)-phenyl]-2-imidazolidinone in racemic or optically active form, optionally separating the latter into its two optically active isomers and hydrolyzing the latter to obtain the product of formula I wherein X is =O or 4-(hydroxymethyl)-4-methyl-1-[4-nitro-3-(trifluoromethyl)-phenyl]-2,5-imidazolidine-dione in racemic or optically active form and optionally separating the latter into its optically active isomers.

Preferably, the reaction of 2-amino-2-(hydroxymethyl)-propane-nitrile and of 3-trifluoromethyl-4-nitrophenyl isocyanate is effected in a solvent such as dichloroethane, but tetrahydrofuran, ethyl ether or isopropyl ether can also be used. It is preferred to operate at ambient temperature without the addition of another reagent.

In a variation of the process, there can also be used 2-amino-2-(hydroxymethyl)-propane-nitrile of which the hydroxy radical is protected by R which is easily eliminated by acid hydrolysis.

After reaction with 3-trifluoromethyl-4-nitro-phenyl isocyanate, there is obtained an intermediate compound of the formula

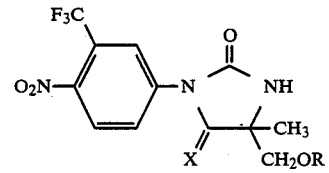   B in which =x is imino and R is a protective group of the hydroxy and the latter is submitted to an acid hydrolysis to obtain a compound of formula I in which X is oxygen.

Examples of R are trityl, silyl, tert.-butyl and groups of the formula

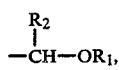

$R_1$ and $R_2$ are individually optionally substituted alkyl or cycloalkyl. R preferably is methoxymethyl, tetrahydrofuryl or tetrahydropyrannyl. In the variation of the process, the protective group is preferably tetrahydropyrannyl and the acid hydrolysis is effected with hydrochloric acid at reflux.

The optional resolution of the racemic product of formula I in which X is imino which racemic product is obtained when starting from racemic 2-amino-2-(hydroxymethyl)-propane-nitrile is done in the usual conditions. For example, a hemisuccinate of formula I can be prepared and the hemisuccinate can be resolved by an optically active base such as ephedrine. The racemic product of formula I can also be condensed with an optically active lactol in an organic solvent and then the two diastereoisomeric ethers can be separated by the usual methods, for example, by chromatography or by crystallization, and finally each of these diastereoisomers can be cleaved in an acid medium to obtain the optically active isomers of the compound of formula I.

In a variation of the process, 2-amino-2-(hydroxymethyl)propane-nitrile with the hydroxy protected by R of the formula

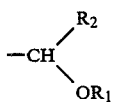

wherein $R_1$ and $R_2$ have the above definitions may be used. The compound has an asymmetric carbon, and either the optically active isomers are separated, if desired, and each isomer is submitted to the reactions indicated above to obtain the optically active isomers of the product of formula I in which X is oxygen, or it is reacted with 3-trifluoromethyl-4-nitrophenyl isocyanate to obtain the intermediate compound which, if desired, the optically active isomers are separated and then each isomer is submitted to an acid hydrolysis to obtain the optically active isomers of the product of formula I in which X is oxygen.

The hydrolysis of the product of formula I in which X is imino into a product of formula I in which X is oxygen is preferably done in the presence of an acid such as hydrochloric acid or sulfuric acid. The eventual resolution of the product of formula I in which X is oxygen when the product is in the racemic form, because it results from the hydrolysis of a racemic product of formula I in which =x is imino is done in the same conditions as the resolution of the same product. Starting from 2-amino-2-(hydroxymethyl)-propane-nitrile in the optically active form, the optical isomer of the starting product is normally retained during the synthesis.

2-amino-2-(hydroxymethyl)-propane-nitrile is prepared from hydroxyacetone by reaction with sodium cyanide, preferably in the presence of ammonium sulfate. The optical resolution of the racemic product obtained is effected by an asymmetric acid such as tartaric acid or one of its derivatives, such as dibenzoyltartaric or paratolyltartaric acid.

It is believed that 2-amino-2-(hydroxymethyl)-propane nitrile in racemic or optically active form is a new product. Like the product RU 23908, the products of formula I and particularly product A in racemic or optically active form, are endowed with interesting pharmacological properties. Particularly, they inhibit the effects of androgens on the peripheral receptors without being a hypophysial inhibitor. Tests in the experimental part illustrate this antiandrogen activity in the rat.

The novel antiandrogenic compositions of the invention are comprised of an antiandrogenically effective amount of at least one compound of formula I and an inert pharmaceutical carrier or excipient. The compositions may be in the form of tablets, dragees, gelules, capsules, suppositories or injectable solutions or suspensions.

Because of their antiandrogenic activity and their lack of effect on the hypophysial function, the compounds of formula I can be used in therapeutics in adolescents without fear of retarding growth and in adults without fear of certain effects of a chemical castration.

The products of formula I and particularly product A in its racemic or optically active form are useful as medicaments for the treatment of adenomas and neoplasia of the prostate, of hirsutism, of acne, of seborrhoea and of hyperpilosity. Like RU -23908, the products of formula I and especially product A are used preferably in the treatment of adenomas and neoplasias of the prostate.

Like RU 23908, the products of formula I and especially ,roduct A can be associated with peptides of the LH-RH type with agonist or antagonist activity in the treatment of adenocarcinomas of the prostate and of benign hypertrophy of the prostate, of endometriosis, of dysmenorrhoea, of hirsutism and of hormono-dependent mammary tumors. A description of these peptides of the type LH-RH is found, for example, in French Pat. BF. 2,465,486.

Thus, the invention also has as its object a composition comprising at least one substance of LH-RH type with agonist or antagonist activity, preferably agonist, and at least one compound of formula I, preferably product A, as a combination for use simultaneously, separately or extended in time in the treatment of adeno-carcinomas of the prostate, of benign hypertrophy of the prostate, of endometriosis, of dysmennorrhoea, of hirsutism and of hormono-dependent mammary tumors, and preferably, of adeno-carcinomas of the prostate.

Furthermore, the presence of androgen receptors has been described in the cancerous cells of a certain number of organs. For example, the following publications can be cited:
tumor of the bladder:
Urology 1985, February Vol. 25 (2) pp. 161-3.
tumor of the brain:
J. Neurooncology 1983, Vol. 1 (3) pp. 179-89.
tumor of the breast:
Cancer 1984, Dec. 1, Vol. 54 (11) pp. 2436-2440
lymphoma:
J. Steroid Biochemistry, 1984, October, Vol. 21 (4), pp. 421-6.
tumor of the kidney:
Cancer 1983, Aug. 1, Vol. 54 (3) pp. 477-81.
tumor of the liver:

Br. J. Cancer 1983, December, Vol. 48 (6) pp. 791–6.
melanoma:
Br. J. Dermatol. 1982 November, Vol. 107, supp. 23, pp. 54–9.
tumor of the ovaries:
J. Endocrinol. 1981 September, Vol 90 (3) pp. 421–31.
tumor of the testicles:
J. Steroid Biochem. 11, 261–265. 1979.
cancer of the lung:
Cancer Res. 45, 4206–4214, 1985.
tumor of the thyroid:
Surgery 96, 996–1000, 1984.
carcinoma of the larynx:
Arch. Otolaryngol. 110, 721–724, 1984.
sarcoma of the soft tissue:
Cancer Res. 40, 861–865, 1980.

The publication Cancer 1984 Aug. 1, Vol. 54 (3) pp. 477–81 describes the absence of activity of Flutamide (2-methyl-N-[4-nitro-3-(trifluoromethyl)-phenyl-propanamide] in the renal carcinoma.

The products of formula I and especially product A in racemic or optically active form can therefore be used alone or in combination for the treatment of hormono-dependent and particularly androgeno-dependent cancers other than that of the prostate. There can also be mentioned cancers affecting the following organs: bladder, brain, breast, lymphatic system, kidney, liver, skin or ovaries.

The pharmaceutical compositions used can be present in the form of injectable suspensions, coated tablets, capsules, suppositories, dermic preparations or forms with controlled release. These compositions are prepared in standard ways. Reference can be made, for example, to the French Pat. No. 2,329,276.

The novel method of the invention for inducing antiandrogenic activity in warm-blooded animals, including humans, comprises administering to warm-blooded animals an anti-androgenically effective amount of at least one compound of formula I. In the uses indicated above, the products of formula I can be administered by parenteral, oral, perlingual, percutaneous or rectal route. The route preferred is orally or percutaneously and the usual daily dose is 1.3 to 66.6 mg/kg depending on the compound administered, the condition treated and the method of administration. For example, the daily oral dose is 0.1 to 20 mg/kg, preferably 0.1 to 5 mg/kg.

In the following examples there are described several preferred embodiments to illustrate the invention. However, it should be understood that the invention is not intended to be limited to the specific embodiments.

EXAMPLE 1

4-(hydroxymethyl)-5-imino-4-methyl-1-[4-nitro-3-(trifluoromethyl)-phenyl]-2-imidazolidinone STEP A: 2-amino-2-(hydroxymethyl)-propane nitrile 305.5 g of ammonium sulfate were added to a solution of 91.2 g of sodium cyanide in 228 ml of demineralized water and the suspension was stirred for 30 minutes, then cooled to +10° C. 175 g of hydroxyacetone were added over 30 minutes, and after standing for 30 minutes at 10° C., the temperature was allowed to rise over 90 minutes, followed by adding 300 ml of ethyl acetate with vigorous stirring and evaporation to dryness. The crystals were taken up in 700 ml of ethyl acetate, stirred for 30 minutes, separated and rinsed three times with 150 ml of ethyl acetate. The mother-liquors were evaporated to dryness to obtain 170 g of product to which 340 ml of dichloromethane were added. After stirring, crystallization was initiated, and the mixture stood for 1 hour at 20° C. and then over night at 5° C. with stirring under nitrogen. The crystals were separated and rinsed with 40 ml and twice with 20 ml of dichloromethane at +10° C. to obtain 47.6 g of the expected product melting at 74° C.

STEP B: 4-(hydroxymethyl)-5-imino-4-methyl-1-[4-nitro-3-(trifluoromethyl)-phenyl]-2-imidazolidinone A solution of 113.4 g of 3-trifluoromethyl-4-nitro-phenylisocyanate in 1800 ml of dichloroethane was stirred for 15 minutes and then, 45 g of 2-amino-2-(hydroxymethyl)-propanenitrile of Step A were added over 15 minutes at 20° C. After stirring for over night, the solvent was eliminated. The residue was rinsed with dichloroethane and after 2 liters of dichloroethane were added, the mixture was refluxed. The blocks formed were ground up, allowed to cool to 25° C., then cooled to 0° C. The insoluble matter was separated, rinsed three times with 100 ml of dichloroethane and then dried under vacuum to obtain 107.5 g of crystals. The crystallized product was ground up and added to 2140 ml of dichloroethane with 10% of methanol. The suspension was refluxed and active carbon was added to the solution which was filtered hot and the mother-liquors were frozen.

The precipitate was separated, rinsed twice with 80 ml of dichloroethane with 10% of methanol and the crystals obtained were dried to obtain 32.7 g of product. The mother-liquors were distilled under vacuum to about 1 liter and vacuum filtered. The precipitate was rinsed three times with 25 ml of dichloroethane to obtain 51.3 g of product which was taken up in 400 ml of dichloroethane with 10% of methanol. The suspension was refluxed, cooled to 20° C., left for 15 minutes and then the precipitate was separated and rinsed twice with 40 ml of dichloroethane with 10% of methanol to obtain 34.1 g of expected product for a total yield of 66.8 g of product melting at 170° C.

EXAMPLE 2

4-(hydroxymethyl)-4-methyl-1-[4-nitro-3-(trifluoromethyl)-phenyl]-2,5-imidazolidine-dione A suspension of 69.7 g of the product of Example 1 in 500 ml of hydrochloric acid diluted 50% was refluxed and a partial solution appeared, then a precipitate. After refluxing for 90 minutes, the mixture was cooled for 2 hours at about 5° C. The insoluble matter was separated, then rinsed 7 times with 70 ml of demineralized water (final pH 6–7) to obtain 67.9 g of the expected product in the form of white crystals melting at 226° C.

EXAMPLE 3

5-(hydroxymethyl)-5-methyl-3-[4-nitro-3-(trifluoromethyl)-phenyl]-2,4-imidazolidine-dione (isomers (+) and (−)

STEP A: (12R)-(−)-5-[[[9,10,11,12,14,15-hexahydro-9,10[3',4']-furano-anthracen-12-yl]-oxy]-methyl]-5-methyl-3-(4-nitro-3-trifluoromethyl-phenyl)-2,4-imidazolidine-dione and (12R)-(+)-5-[[[9,10,11,12,14,15-hexahydro-9,10[3',4']-furanoanthracen-12-yl]oxy]-methyl]-5-methyl-3-(4-nitro-3-trifluoromethyl-phenyl)-2,4-imidazolidine-dione and (12R)-(+)-5-[[[9,10,11,12,14,15-hexahydro-9,10[3',4']-furanoanthracen-12-yl]-oxy]-methyl]-5-methyl-3-(4- nitro-3-trifluoromethyl-phenyl)-2,4-imidazolidine-dione.

Under an inert atmosphere, 11 g of the racemic product of Example 2 in 500 ml of tetrahydrofuran was refluxed for 10 minutes in the presence of 5.5 g of p-toluene sulfonic acid and then, over two-and-a-half hours, a solution of 11 g of anthracenic lactol (S) in 500 ml of tetrahydrofuran was added. After refluxing for 3 hours, the solvent was eliminated under reduced pressure, and the residue was chromatographed on silica (eluent:cyclohexane—ethyl acetate, 1-1, then flugene—tetrahydrofuran 7-3) to obtain 1.8 g of the isomer 12R(−) and 0.8 g of the isomer 12R(+) as well as 2.2 g of a mixture which was chromatographed again (eluent:flugene-tetrahydrofuran 7-3) to obtain a further 0.3 g of isomer 12R(−) and 1 g of isomer 12R(+).

STEP B: 5-(hydroxymethyl)-5-methyl-3-[4-nitro-3-(trifluoromethyl)-phenyl]-2,4-imidazolidine-dione, isomers (+) and (−)

1.378 g of the isomer 12R (+) of Step A in 21 ml of dioxane, 0.3 g of p-toluene sulfonic acid and 10 ml of water were refluxed for one-and-a-half hours. The solvents were eliminated under reduced pressure and the residue was chromatographed on silica (eluent:methylene chloride-acetone, 8-2) to obtain 0.51 g of crude product which was crystallized from ether to obtain 0.453 g of the expected isomer (+).

Using the same procedure starting from the diastereoisomer 12R (−), the expected isomer (−) was obtained.

Isomer (+): $[\alpha]_D = +44.5 \pm 1.5$ (c=0.75% in methanol).

Analysis: $C_{12}H_{10}F_3O_5N_3$; molecular weight=333.226: Calculated: %C 43.25; %H 3.02; %N 12.61; %F 17.10. Found: %C 43.2; %H 2.9; %N 12.6; %F 17.0.

Isomer (−): $[\alpha]_D = -40 \pm 1.5$ (c=0.8% in methanol).

Analysis: Calculated: %C 43.25; %H 3.02; %N 12.61; %F 17.10. Found: %C 43.1; %H 2.9; %N 12.6; %F 17.2.

Pharmacological study of
4-(hydroxymethyl)-4-methyl-1-[4-nitro-3-(trifluoromethyl)-phenyl]-2,5-imidazolidine-dione (Product A)

Antiandrogen activity in the rat was determined using groups of 5 male rats weighing about 100 g, castrated 24 hours before the start of the treatment. They received subcutaneously every day for eight days product A [2, 10 or 50 mg/kg combined with 0.5 mg/kg of testosterone propionate (T.P.)] in a volume of 2.5 ml/kg of sesame oil containing 5% of benzyl alcohol. A group of castrated animals acted as control and received only the solvent. The animals were killed 24 hours after the last treatment and the seminal vesicles and the prostate were removed and stirred for 24 hours in a 10% solution of Formol in water, then dissected and weighed. The increase in weight of the organs or the inhibition of the effect induced by the testosterone propionate expressed respectively, the androgen or antiandrogen activity of the products. The following results were obtained:

| Groups | Seminal vesicles weight in mg. | % inhibition of the weight of the seminal vesicles | ventral prostate weight in mg. | % inhibition of the prostate weight. |
|---|---|---|---|---|
| Witnesses | 13.6 ± 0.9 | — | 22.4 ± 1.2 | — |
| Testosterone propionate | | | | |
| T.P. 0.5 mg | 120.7 ± 15.4 | — | 133.9 ± 10.1 | — |
| T.P. 0.5 mg +2 mg of product A | 82.3 ± 10.8 | 35.7 | 121.6 ± 8.1 | 11 |
| T.P. 0.5 mg +10 mg of product A | 42.8 ± 6.0 | 72.7 | 70.8 ± 11.8 | 56.6 |
| T.P. 0.5 mg +50 mg of product A | 22.0 ± 3.2 | 92.1 | 50.9 ± 5.6 | 74.4 |

CONCLUSION

Product A of in Example 2 presents a good antiandrogen activity vis-à-vis testosterone propionate.

Various modifications of the products and methods of the invention may be made without departing from the spirit or scope thereof and it is to be understood that the invention is intended to be limited only as defined in the appended claims.

What we claim is:

1. A compound in all possible racemic and optically active forms of the formula

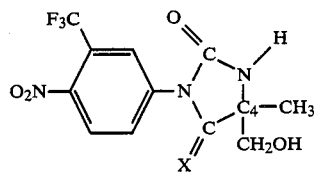

wherein =x is =O or imino.

2. A compound of claim 1 which is 4-(hydroxymethyl)-5-imino-4-methyl-1-[4-nitro-3-(trifluoromethyl)-phenyl]-2-imidazolidinone in racemic or optically active form.

3. A compound of claim 1 which is 4-(hydroxymethyl)-4-methyl-1-[4-nitro-3-(trifluoromethyl)-phenyl]-2,5-imidazolidine-dione in racemic or optically active form.

4. A compound of claim 1 which is (4R) 4-(hydroxymethyl)-4-methyl-1-[4-nitro-3-(trifluoromethyl)-phenyl]-2,5-imidaZolidine-dione.

5. A compound of claim 1 which is (4S) 4-(hydroxymethyl)-4-methyl-1-[4-nitro-3-(trifluoromethyl)-phenyl]-2,5-imidazolidine-dione.

6. A compound of claim 1 which is 4-(hydroxymethyl)-4-methyl-1-[4-nitro-3-(trifluoromethyl)-phenyl]-2,5-imidazolidine-dione in the form of a mixture of isomers (4R) and (4S).

7. An antiandrogenic composition comprising an antiandrogenically effective amount of at least one compound of claim 1 and an excipient.

8. A composition of claim 7 wherein the active compound is 4-(hydroxymethyl)-5-imino-4-methyl-1-[4-nitro-3-(trifluoromethyl)-phenyl]-2-imidazolidinone in racemic or optically active form.

9. A composition of claim 7 wherein the active compound is 4-(hydroxymethyl)-4-methyl-1-[4-nitro-3-(trifluoromethyl)-phenyl]-2,5-imidazolidine-dione in racemic or optically active form.

10. A composition of claim 7 wherein the active compound is (4R) 4-(hydroxymethyl)-4-methyl-1-[4-nitro-3-(trifluoromethyl)-phenyl]-2,5-imidazolidine-dione.

11. A composition of claim 7 wherein the active compound is (4S) 4-(hydroxymethyl)-4-methyl-1-[4-nitro-3-(trifluoromethyl)-phenyl]-2,5-imidazolidine-dione.

12. A composition of claim 7 wherein the active compound is 4-(hydroxymethyl)-4-methyl-1-[4-nitro-3-(trifluoromethyl)-phenyl]-2,5-imidazolidine-dione in the form of a mixture of isomers (4R) and (4S).

13. A method of inducing antiandrogenic activity in warm-blooded animals comprising administering to warm-blooded animals an antiandrogenically effective amount of at least one compound of claim 1.

14. The method of claim 13 wherein the compound is 4-(hydroxymethyl)-5-imino-4-methyl-1-[4-nitro-3-(trifluoromethyl)-phenyl]-2-imidazolidinone in racemic or optically active form.

15. The method of claim 13 wherein the compound is 4-(hydroxymethyl)-4-methyl-1-[4-nitro-3-(trifluoromethyl)-phenyl]-2,5-imidazolidine-dione in racemic or optically active form.

16. The method of claim 13 wherein the compound is (4R) 4-(hydroxymethyl)-4-methyl-1-[4-nitro-3-(trifluoromethyl)-phenyl]-2,5-imidazolidine-dione.

17. The method of claim 13 wherein the compound is (4S) 4-(hydroxymethyl)-4-methyl-1-[4-nitro-3-(trifluoromethyl)-phenyl]-2,5-imidazolidine-dione.

18. The method of claim 13 wherein the compound is 4-(hydroxymethyl)-4-methyl-1-[4-nitro-3-(trifluoromethyl)-phenyl]-2,5-imiazolidine-dione in the form of a mixture of isomer (4R) and (4S).

* * * * *